(12) United States Patent
Timar et al.

(10) Patent No.: US 8,486,707 B2
(45) Date of Patent: Jul. 16, 2013

(54) METHOD OF OLIGONUCLEOTIDE SEQUENCING BY MASS SPECTROMETRY

(75) Inventors: Zoltan Timar, Loveland, CO (US); Gergo Hegedus, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 101 days.

(21) Appl. No.: 13/093,723

(22) Filed: Apr. 25, 2011

(65) Prior Publication Data

US 2012/0100623 A1    Apr. 26, 2012

Related U.S. Application Data

(60) Provisional application No. 61/328,095, filed on Apr. 26, 2010.

(51) Int. Cl.
*H01J 49/26* (2006.01)
*G01N 21/00* (2006.01)
*G06F 19/00* (2006.01)

(52) U.S. Cl.
USPC .............. 436/94; 436/93; 436/91; 422/82.05; 422/68.1; 422/50; 702/19; 702/1

(58) Field of Classification Search
USPC .................... 436/94, 93, 91; 422/82.05, 68.1, 422/50; 702/19, 1
See application file for complete search history.

(56) References Cited

U.S. PATENT DOCUMENTS 6,017,693 A  1/2000 Yates et al.
6,624,408 B1  9/2003 Franzen

OTHER PUBLICATIONS

Drexler, et al., "Automated identification of isotopically labelled pesticides and metabolites by intelligent real-time liquid chromatography-tandem mass spectrometry using a bench-top ion trap", Rapid Commun. Mass Spectrom., 1998, 12:1501-1507.
Eng, "An approach to correlate tandem mass spectral data of peptides with amino acid sequences in a protein database", J Am Soc Mass Spectrom, 1994, 5:976-989.
McLuckey, et al., "Tandem mass spectrometry of small, multiply charged oligonucleotides", J Am Soc Mass Spectrom, 1992, 3:60-70.
Oberacher, et al., "On the use of ESI-QqTOF-MS/MS for the comparative sequencing of nucleic acids", Biopolymers, 2009, 91:401-9.
Rozenski, et al., "SOS: a simple interactive program for ab initio oligonucleotide sequencing by mass spectrometry", J Am Soc Mass Spectrom, 2002, 13:200-3.
Sannes-Lowery, et al., "Sequence confirmation of modified oligonucleotides using IRMPD in the external ion reservoir of an electrospray ionization Fourier transform ion cyclotron mass spectrometer", J Am Soc Mass Spectrom, 2003, 14:825-33.
Snider, "Efficient calculation of exact mass isotopic distributions", Author Manuscript, J Am Soc Mass Spectrom, 2007, 18:1-12.
Snider, "Efficient calculation of exact mass isotopic distributions", J Am Soc Mass Spectrom, 2007, 18:1511-5.

*Primary Examiner* — Christine T Mui

(57) ABSTRACT

A computer-implemented method for confirming the nucleotide sequence of an oligonucleotide is provided. In certain embodiments, the method comprises: a) inputting the nucleotide sequence of an oligonucleotide; b) executing an algorithm that provides the predicted molecular formulas of fragments of the oligonucleotide; c) comparing the predicted m/z values of the predicted molecular formulas to experimentally-obtained m/z values obtained by analysis of the oligonucleotide by tandem mass spectrometry to determine if the predicted masses correspond with the experimentally-obtained masses. The method may be used, for example, to confirm the identity of an oligonucleotide after it is synthesized.

15 Claims, 9 Drawing Sheets

METHOD OF OLIGONUCLEOTIDE SEQUENCING BY MASS SPECTROMETRY

CROSS-REFERENCING

This application claims the benefit of provisional application Ser. No. 61/328,095, filed on Apr. 26, 2010, which application is incorporated herein in its entirety for all purposes.

INTRODUCTION

Synthetic oligonucleotides may be employed for a number of applications, including therapeutic applications (e.g., as inhibitory RNAs) and research applications (e.g., as probes or as primers). This disclosure relates in part to a method for confirming the nucleotide sequence of an oligonucleotide after synthesis.

SUMMARY OF THE INVENTION

A computer-implemented method for confirming the nucleotide sequence of an oligonucleotide is provided. In certain embodiments, the method comprises: a) inputting the nucleotide sequence of an oligonucleotide; b) executing an algorithm that provides the predicted molecular formulas of fragments of the oligonucleotide; c) comparing the predicted m/z values of the predicted molecular formulas to experimentally-obtained m/z values obtained by analysis of the oligonucleotide by tandem mass spectrometry to determine if the predicted masses correspond with the experimentally-obtained masses. The method may be used, for example, to confirm the identity of an oligonucleotide after it is synthesized, i.e., to confirm that it has the expected sequence.

DEFINITIONS

Figure 1:
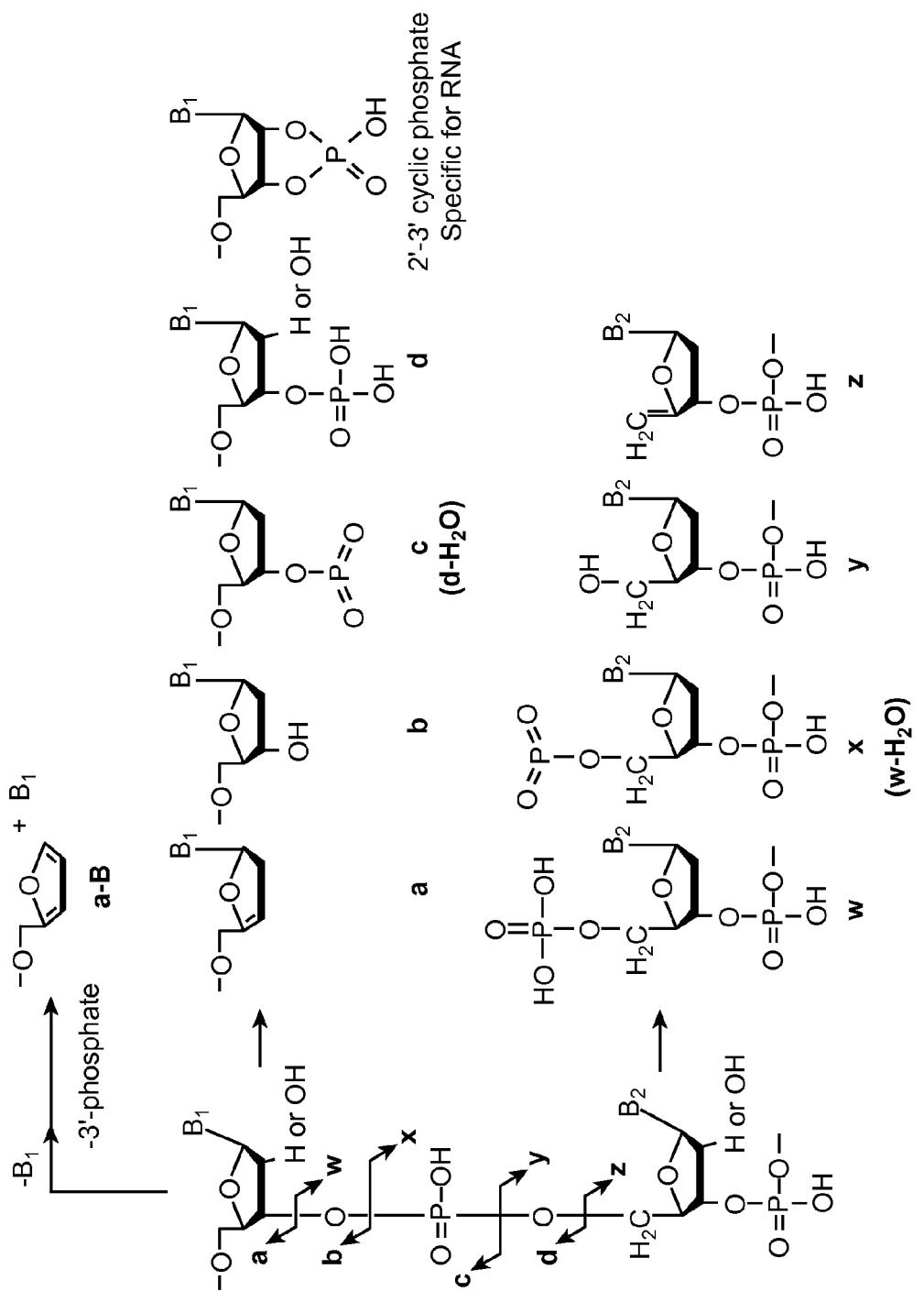
FIG. 1 shows the nomenclature of oligonucleotide fragments by McLuckey et al. Ion species are negatively charged in the $(M-nH)^{n-}$ type series. $B_n$: nucleobase at position n. The original naming of a-B ions included the position as subscript of "a" such as $a_7$-B, where B is lost from position 7 as well, thus we use $(a-B)_7$ for this type hereafter. $B_1$, lost in forming the a-B ion fragment, denotes either charged (positively by protonation or negatively by deprotonation) or neutral nucleobase species. 'c'-fragments are also named as "d-$H_2O$" and "x" as "w-$H_2O$" by different research groups. "c"-type RNA fragments are likely in their cyclic phosphate form.

The term "oligonucleotide" as used herein denotes a synthetic (i.e., machine-made) single stranded multimer containing from about 2 to 500 nucleotides. In some embodiments, are 10 to 50 nucleotides in length. Oligonucleotides may contain ribonucleotide monomers (i.e., may be oligoribonucleotides) or deoxyribonucleotide monomers or a combination of ribonucleotide or deoxyribonucleotide monomers. Oligonucleotides may be 10 to 20, 21 to 30, 31 to 40, 41 to 50, 51-60, 61 to 70, 71 to 80, 80 to 100, 100 to 150, 150 to 200 or greater than 200 nucleotides in length, for example.

The term "nucleotide" is intended to include those moieties that contain not only the known purine and pyrimidine bases found in naturally-occurring DNA and RNA, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. An oligonucleotide may also contain components not found in nucleic acid found in nature, e.g., a linker, labels (e.g., biotin or a linked fluorescent dye), and other modifications (phosphate groups, glycosylation, etc).

A "tandem" mass spectrometer is a mass spectrometer that is capable of isolating precursor ions, fragmenting the precursor ions, and analyzing the fragmented precursor ions. Such systems are well known in the art (see, e.g., U.S. Pat. Nos. 7,534,996, 7,531,793, 7,507,953, 7,145,133, 7,229,834 and 6,924,478) and may be implemented in a variety of configurations. In certain embodiments, tandem mass spectrometry may be done using individual mass analyzers that are separated in space or, in certain cases, using a single mass spectrometer in which the different selection steps are separated in time. Tandem MS "in space" involves the physical separation of the instrument components (QqQ or QTOF) whereas a tandem MS "in time" involves the use of an ion trap tandem mass spectrometry. Oligonucleotides may be fragmented in the gas phase by collisionally induced dissociation (CID) using a QTOF mass spectrometer or in the source using increased fragmentor potential.

The terms "system" and "computer-based system" refer to the hardware means, software means, and data storage means used to analyze the information of the present invention. The minimum hardware of the computer-based systems of the present invention comprises a central processing unit (CPU), input means, output means, and data storage means. As such, any convenient computer-based system may be employed in the present invention. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Computer readable medium" as used herein refers to any physical, tangible storage or transmission medium that participates in providing instructions and/or data to a computer for execution and/or processing. Examples of storage media include floppy disks, magnetic tape, UBS, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory. A computer readable medium is physical and is not a signal.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable. To "record" data, programming or other information on a computer readable medium refers to a process for storing information, using any convenient method. Any convenient data storage structure may be chosen, based on the means used to access the stored information. A variety of data processor programs and formats can be used for storage, e.g. word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives, and solid state memory devices).

In certain embodiments, a system includes hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include Windows, MacOS, Sun Solaris, Linux, OS/400, Compaq Tru64 Unix, SGI IRIX, Siemens Reliant Unix, and others. The functional elements of system may also be implemented in accordance with a variety of software facilitators, platforms, or other convenient method.

Items of data are "linked" to one another in a memory when the same data input (for example, filename or directory name or search term) retrieves the linked items (in a same file or not) or an input of one or more of the linked items retrieves one or more of the others.

Subject computer readable media may be at a "remote location", where "remote location," means a location other than the location at which the MALDI ionization and detection apparatus. For example, a remote location could be another location (e.g., office, lab, etc.) in the same city, another location in a different city, another location in a different state, another location in a different country, etc. As such, when one item is indicated as being "remote" from another, what is meant is that the two items may be in the same room but separated, or at least in different rooms or different buildings, and may be at least one mile, ten miles, or at least one hundred miles apart.

"Communicating" information references transmitting the data representing that information as, e.g., electrical or optical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the Internet or Intranets including email transmissions and information recorded on websites and the like.

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The following references are incorporated by references in their entireties for all purposes: McLuckey et al (*Tandem mass spectrometry of small, multiply charged oligonucleotides*. Journal of the American Society for Mass Spectrometry, 1992. 3(1): p. 60-70); Oberacher (*On the Use of ESI-QqTOF-MS/MS for the Comparative Sequencing of Nucleic Acids*. Biopolymers, 2009. 91: 401-409); Rozenski, J. and J. A. McCloskey, (*SOS: a simple interactive program for ab initio oligonucleotide sequencing by mass spectrometry* Journal of the American Society for Mass Spectrometry, 2002. 13: 200-203), Oberacher, H., B. Wellenzohn, and C. G. Huber, (*Comparative sequencing of nucleic acids by liquid chromatography-tandem mass spectrometry*. Analytical Chemistry, 2002. 74: 211-218); and Rozenski, J. and J. A. McCloskey, *SOS: a simple interactive program for ab initio oligonucleotide sequencing by mass spectrometry*. Journal of the American Society for Mass Spectrometry, 2002. 13: 200-203); and Snider (*Efficient calculation of exact mass isotopic distributions* J. Am. Soc. Mass Spectrom., 2007, 18, 1511).

A computer-implemented method for confirming the nucleotide sequence of an oligonucleotide comprising: a) inputting the nucleotide sequence of an oligonucleotide; b) executing an algorithm that provides the predicted molecular formulas of fragments of the oligonucleotide; c) comparing the predicted exact mass to charge (m/z) values, that are calculated from the predicted molecular formulas, to experimentally-obtained mass to charge values obtained by analysis of the oligonucleotide by tandem mass spectrometry to determine if the predicted masses correlate with the experimentally-obtained masses is provided. The method may be used, for example, to confirm the identity of a oligonucleotide after it is synthesized, i.e., to confirm that has the expected sequence. In some embodiments, the inputting may comprises inputting the sequence of oligonucleotide that contains one or more nucleotide analogs or, in certain cases, inputting a label moiety or linker that is part of oligonucleotide.

In some cases, the algorithm provides predicted molecular formulas for a-B, a, b, c, d, w, x, y and z fragments of the oligonucleotide, where the bonds broken to obtain those fragments are defined in FIG. 1. In these embodiments, the comparing step may comprise comparing the predicted m/z values for all a-B, a, b, c, d, w, x, y and z fragments of the oligonucleotide to experimentally-obtained m/z values. In some embodiments, the experimentally-obtained m/z values are within a range of m/z values, e.g., in the range of 100 to 5000 mass units.

In some embodiments, the comparison step may result in an editable data file comprising a table that in particular cases may be used to generate a human-readable report based on table. In some cases, the method may further comprise looking at the report in a graphical format, identifying any overlapping peaks, editing the data file and re-performing the correlation step based on the edited data table. In some embodiments, the method may further comprise synthesizing an oligonucleotide; analyzing the oligonucleotide using tandem mass spectrometry; and performing steps a), b) and c) using the nucleotide sequence of the oligonucleotide and data obtained from the analyzing.

A physical computer readable medium is also provided. In certain cases, the medium may comprise programming for: a) inputting the nucleotide sequence of an oligonucleotide; b) predicting the molecular formulas of fragments of the oligonucleotide using an algorithm; c) comparing the predicted mass over charge values from the predicted molecular formulas, to experimentally-obtained m/z values obtained by analysis of the oligonucleotide by tandem mass spectrometry to determine if the predicted m/z values correspond with the experimentally-obtained masses.

In some cases, the algorithm may provide predicted m/z values for a-B, a, b, c, d, w, x, y and z fragments of the oligonucleotide, where the bonds broken to obtain the fragments are defined in FIG. 1. In these embodiments, the programming may provide for comparing the predicted m/z values for all a-B, a, b, c, d, w, x, y and z fragments of the oligonucleotide to experimentally-obtained m/z values. In some embodiments, the physical computer readable medium may be present on a computer and operably linked to a processor for executing the programming.

Also provided is a system comprising: an oligonucleotide synthesizer; a tandem mass spectrometer; and a computer comprising the physical computer readable medium as summarized above.

In certain embodiments the programming summarized above compares calculated sequencing data to mass spectrum data generated on MS/MS analytical instrument (also known as a tandem mass spectrometer). That comparison enables a user to make a decision regarding the identity of a synthesized oligonucleotide. The method does not make a final determination on product sequencing, i.e., does not provide a binary "correct" or "incorrect" output. The tool provides fast and objective compilation of MS/MS data required for highly modified oligonucleotide identification.

Figure 5:
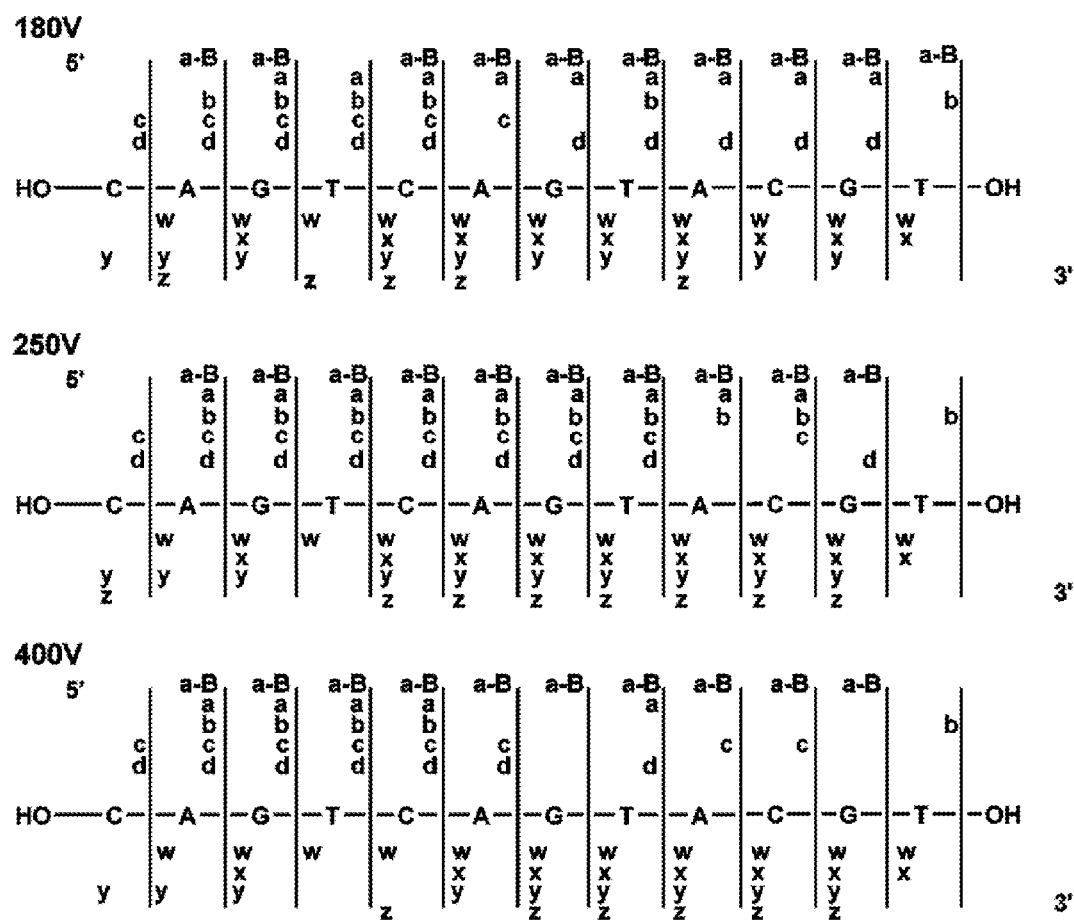
FIG. 5 schematically illustrates a oligonucleotide and the fragments that can be expected therefrom.
Figure 6:
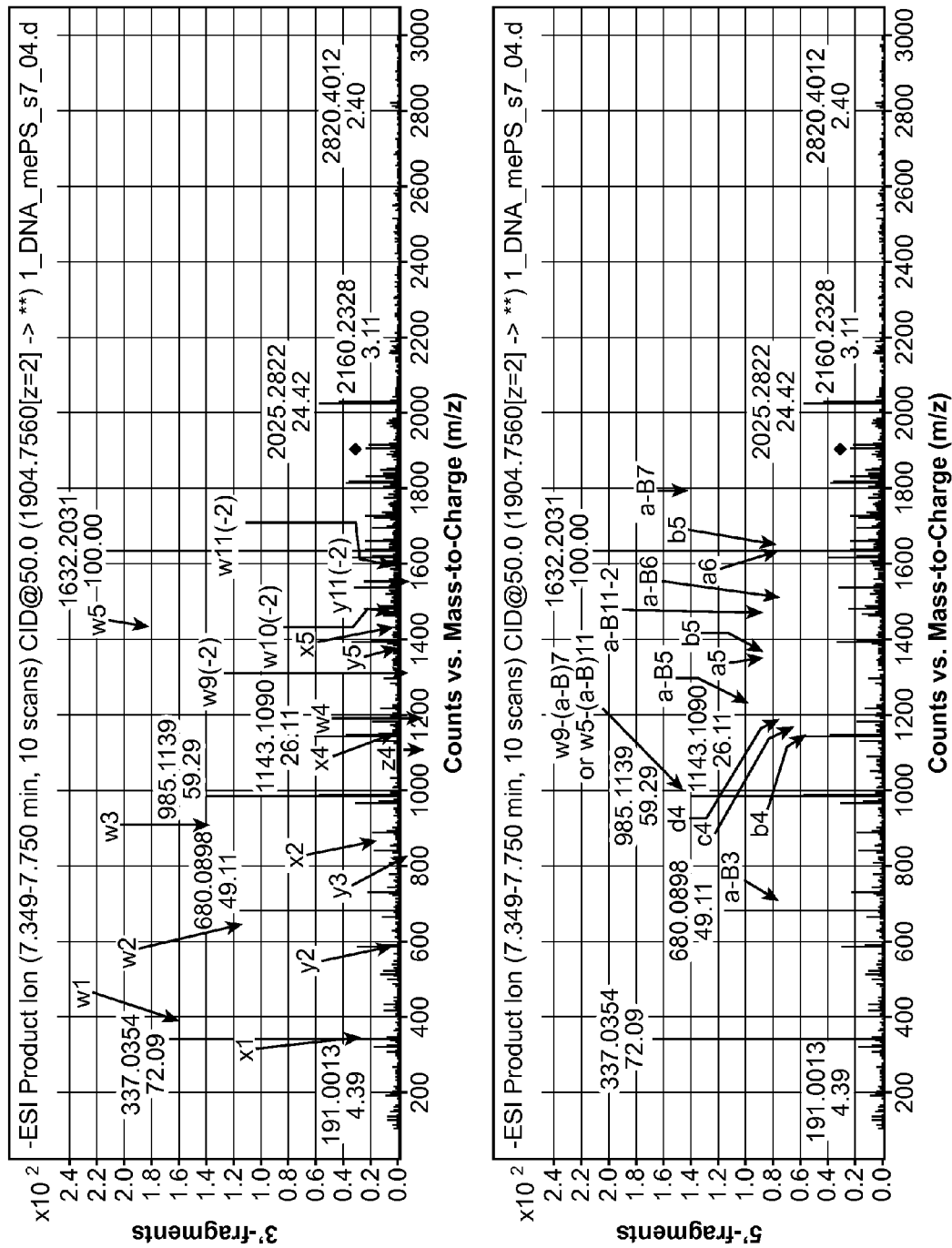
FIG. 6 shows a mass spectrum of fragments of a methyl phosphonate-DNA PS chimera of the following sequence CsAvG[vTsCvAsG]-[sTvAsCvG]-sT.
Figure 7:
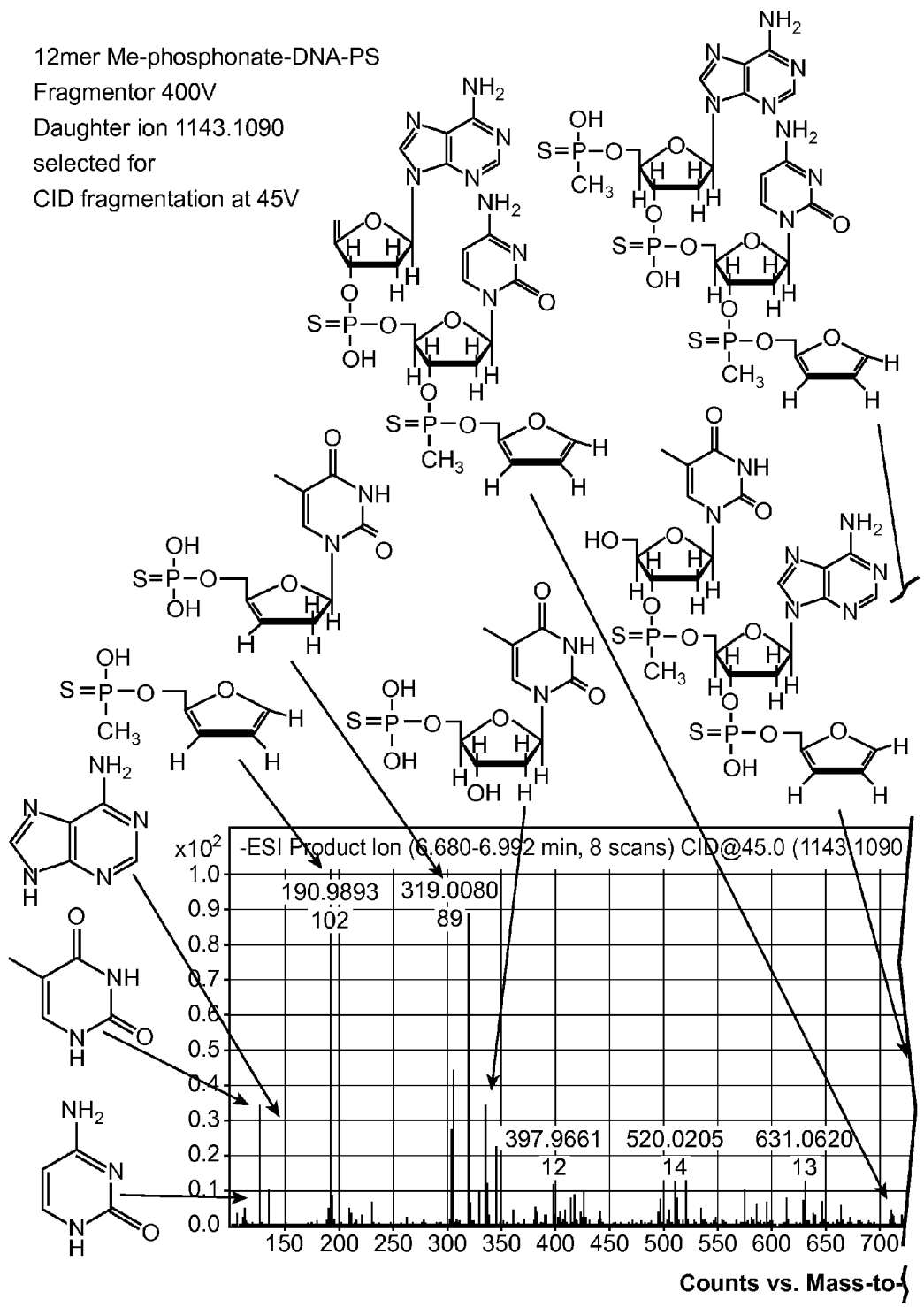
FIG. 7 shows a mass spectrum of the 12 mer Me-phosphonate-DNA-PS, showing that the fragments expected for the oligonucleotide (shown by their chemical formulas) correspond to the molecular masses obtained by analyzing the oligonucleotide by tandem MS.
Figure 7:
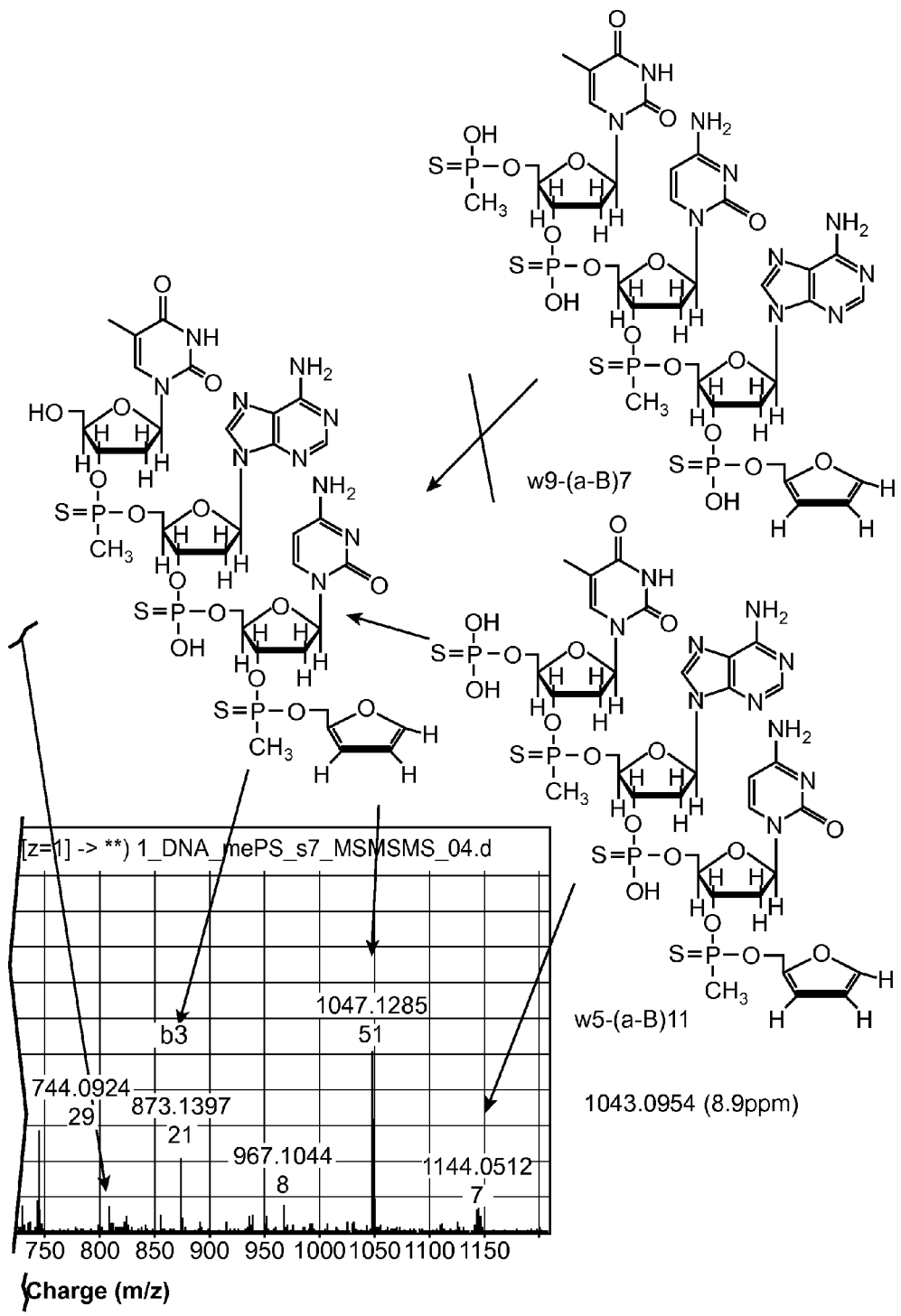

Examples of fragments that can be obtained from an oligonucleotide are shown in FIG. 5. FIG. 6 shows a mass spectrum of fragments of an exemplary oligonucleoitide that is methyl phosphonate-DNA PS chimera of the following sequence CsAvGvTsCvAsGsTvAsCvGsT where capital letters symbolize DNA nucleosides, v stands for methylphosphonate thioate and s is for phosphorothioate diester. FIG. 7 shows a mass spectrum of the 12 mer Me-phosphonate-DNA-PS, showing that the fragments expected for the oligonucleotide (shown by their chemical formulas) correspond to the molecular masses obtained by analyzing the oligonucleotide by tandem MS.

In certain embodiments, the method compares predicted fragment data to MS/MS data generated on a tandem mass spectrometer, e.g., a QTOF such as an Agilent 6520 Accurate-Mass Quadruple Time Of Flight instrument.

Figure 2:
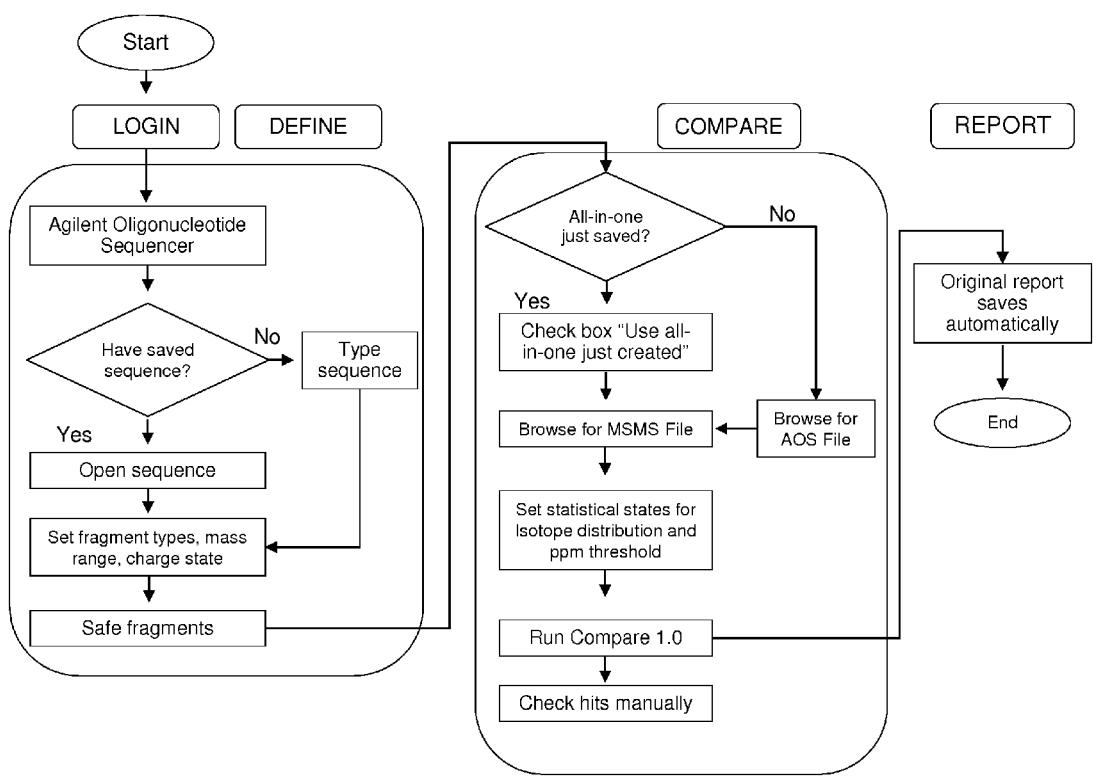
FIG. 2 is a flow chart showing general steps of one embodiment of the method.
Figure 3:
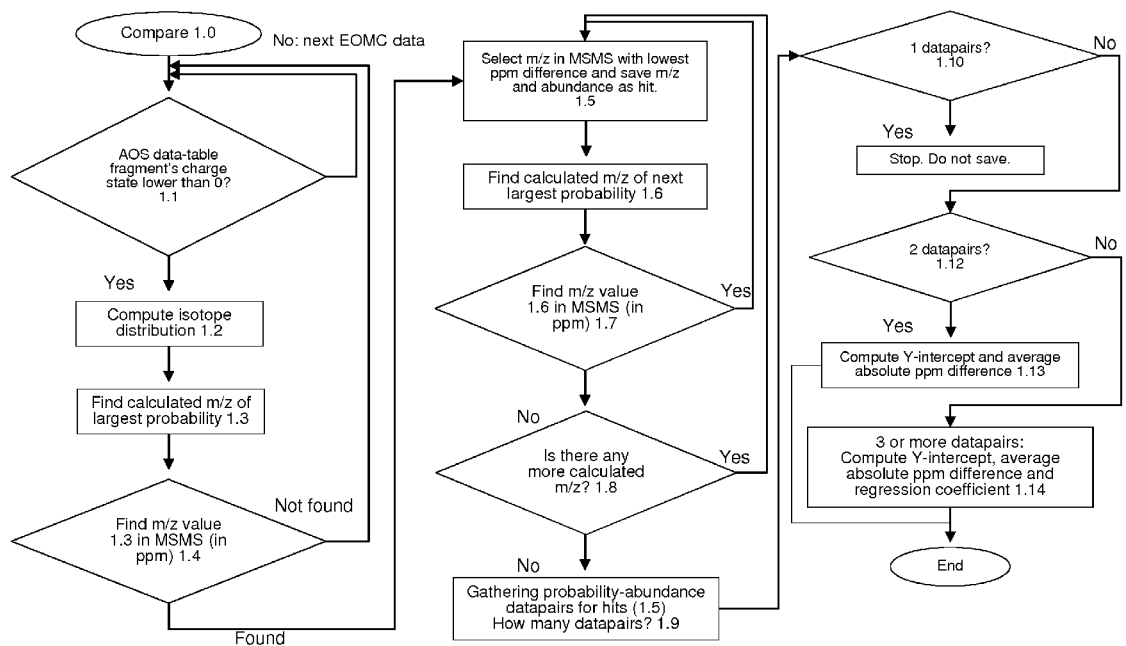
FIG. 3 is a flow chart showing the general steps of the compare function.
Figure 4:
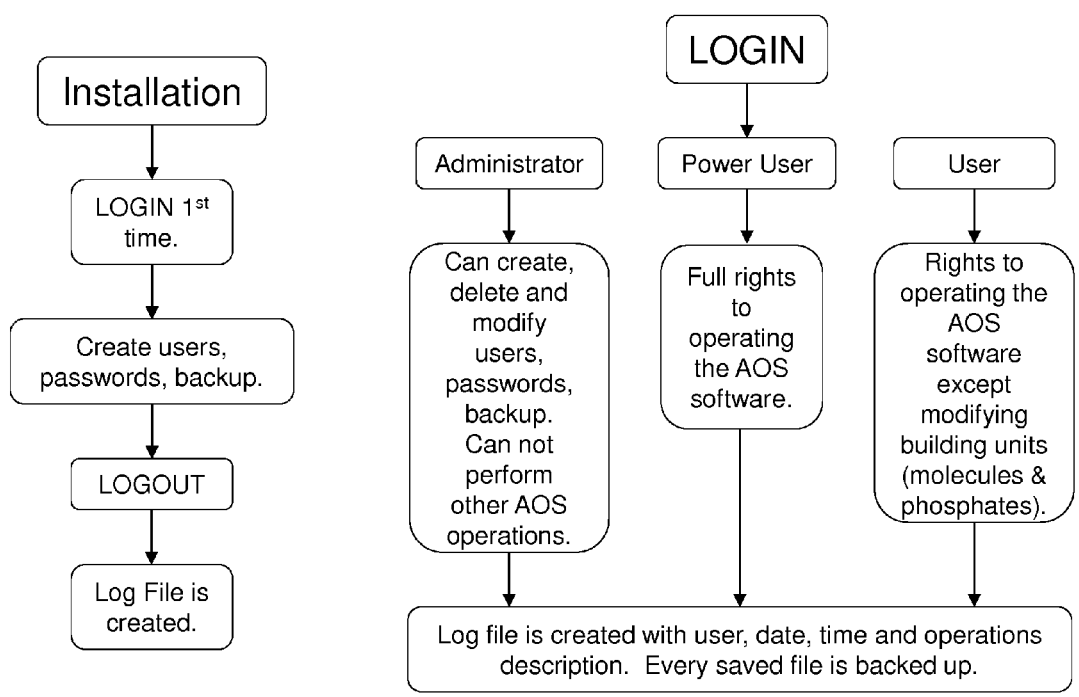
FIG. 4 is a flow chart showing elements of System Installation, Security groups & AOS Audit Trail Functions.

One embodiment of the method is illustrated in general terms in the flowcharts of FIGS. 2-4.

With reference to FIG. 2, the first function is to allow a user to "define" the sequence to be analyzed and generate the fragment table. This function provides the ability to select or define the sequence. This function provides the ability to set the output mass range, charge state, and target fragments. There function also the independent ability to select and define custom molecules. As illustrated, the fragment table may be saved in a .csv format.

With reference to FIG. 3, the third function is to "compare" two selected files: the generated fragment table (i.e., a table containing predicted m/z values) to the MS/MS spectrum (which has experimentally determined m/z values). In this function, the user selects the created file path and the MS/MS file path. The results of the comparison can include formula, fragment name, average ppm difference, correlation function parameters (r and y-intercept), number of data pairs, and an indicator if that item was a "hit", in other words match, and if that was going to be included in the report file. The compare function may also include graphical comparison of matches, as the calculated m/z-probability plot to the matched MS/MS spectral region. In certain cases, the isotope distribution calculation is performed for a number of states, stat by a user, to gain fine resolution exact masses. Averaged (coarse) exact masses are calculated by weight averaging the "x" (mass) values and summing probabilities. Exact mass values are correct with electron masses.

With reference to FIG. 4, the system's third major function is to produce a "report". A full AOS Report lists out the two file names, and then columns for all formulas, the type of fragment along with position and charge state, average ppm difference, r(yy"), y-intercept and notes on the number of data pairs for each. In addition, the system and its SOPs provide the ability for the administrator to manage the AOS Users access rights under change control.

In one embodiment, a QTOF such as Agilent 6500 series QTOF is employed to generate MS/MS (gas phase fragmentation) data on oligonucleotides, and deconvolution of that data is done with the method. One problem with both the MS/MS data and the theoretical gas phase fragmentation of oligonucleotides over a certain size (>10 mers) is that both are highly complicated. The comparison of two complex data sets, without computational support, takes computional effort. The application of the the programming for oligonucleotide MS/MS data interpretation simplifies the problem to minutes of work with no or moderate expertise of mass spectrometry or data interpretation.

A further advantage of some embodiments of the method over existing data interpretation softwares is that it is fully compatible with any kind of oligonucleotides for fragment data table generation and not limited by the type of fragmentation, nucleosides, phosphates or size of the oligonucleotide. The data library of the software is expandable with nucleosides, linkers, modifiers and phosphates by the user. In other words, if a new type of nucleotide is developed, the new nucleotide can be added to data library and the oligonucleotide containing the new nucleotide can immediately be sequenced by the software combined with the a tandem mass spectrometer using e.g., gas phase fragmentation methodology. The method does predict masses for DNA, RNA and unrestricted number of modified nucleosides or phosphates for any length. The method is not limited by the size of oligonucleotide. Moreover, the softwar can calculate the nine different fragment's molecular formulas for every possible position in an oligonucleotide, as well as also calculate theoretical mass spectra for any molecular formula not limited to oligonucleotides.

The method has another major function in that it contains a comparing step. The compare function of the software is capable of comparing and correlating mass spectra calculated from molecular formulas in a special format (fragment data table in an Excel compatible .csv type electronic file format) to a centroid mass spectrum exported from MS or MS/MS analysis. This kind of comparison is for sequence verification only, but the methodology is capable to compare any sequences to any MS (or MS/MS) data file, hence with high enough input sequences, it is possible to use the methodology for de novo sequencing.

The comparing step of the method is based on isotope distribution calculation from a molecular formula. One way of calculating an isotope distribution is published by Sneider (Snider, R. K., J. Am. Soc. Mass Spectrom., 2007, 18, 1511). The algorithm is used to calculate high resolution exact masses for the fragment molecular formulas. The high resolution isotope distribution is first weighed averaged to be compatible with the resolution of the QTOF mass resolution.

From the calculated isotope distribution in the neutral charge state, different charge state mass spectra are calculated and used in the compare function of the software. The exact masses are searched by a user defined ppm constraint in a data file e.g., an Agilent QTOF MassHunter data file. The MS data file is not altered (no deconvolution, charge neutralization) except for converting the profile data to centroid and the threshold (intensity) is set before export. Since the MS data file is not altered and, the comparison of the calculated fragment data table to the MS data file is done by the AOS software, the findings (result hits) are objectively found. The advantage of such methodology that there is no data loss or compromise up to the point of the original findings.

One advantage of certain embodiments of the method is that the first objective set of results can be looked up visually in a graph generating function of the AOS report table. The user can review the findings and override the software findings. The advantage of the user control over the findings is that complex mass spectra can be ambiguous, even high performance mathematical algorithms can fail in deconvolution of overlapping high resolution mass spectra peaks. In contrast, human intelligence can recognize patterns that are overlooked by software, and this advantage is given to the user only on objectively harvested data. In this way, the final results of sequencing is more accurate. Also the results are saved with correlation (statistical) parameters, that support the findings.

The method described below for sequence verification of oligonucleotides may employ oligonucleotide that contain DNA (Adenine, Cytosine, Guanine, Thymine, Uracil, Hypoxanthine), RNA, 2'-methoxy-RNA, 2'-fluoro-RNA, 2'-MOE-RNA, LNA, UNA, 5'-amino-2'-deoxy nucleosides, abasic nucleoside (1'-OH), 1'-2'-dehydro-abasic nucleoside (base loss in gas phase by elimination), linkers (5-aminopentyl, 6-amino-hexyl, triPEG or hexaethylene glycol), modifiers (cholesteryl, biotinyl, fluorescein, Quasar, CPR), or any mixture of the above. Also the above mentioned nucleosides, linkers, modifiers and phosphates might have protecting groups that are not entirely removed at the final cleavage of the product. The method can search for such protecting group containing oligonucleotide fragments. In certain cases, the oligonucleotides may be degraded during the chemical synthesis or during the post synthetic work-up process. Due to the flexibility of building block library of the AOS software, any kind of such chemical modifications or degradations can be defined and searched for by AOS.

In certain cases, the method compares unaltered centroided MS or MS/MS data to a calculated fragment data table using a mass to charge (m/z) search and correlations between accurate MS exact mass data and calculated exact isotope masses, which, combined with user access to overrule the findings can be applied to other linear or branched polymers such as carbohydrates and peptides. The methodology is not limited by the size of the oligomers, only by the performance of mass spectrometer. The method can also be applied to shortmer identification and search for enzymatic and chemical cleavage products of oligonucleotides. The concept of the methodology can be applied to carbohydrate and peptide sequencing by MS/MS, enzymatic or chemical degradation.

EXAMPLES

The following examples are put forth so as to provide those of ordinary skill in the art with further details of an algorithm used in one embodiment of the method and is not intended to limit the scope of what the inventors regard as their invention.

1. Isotope abundance

In order to compare measured and computed m/z values, we need to compute the exact masses & probabilities of a given molecule. Algorithm description is discussed below.

Calculating ion distributions for large molecules require expanding the polynomial of the form:

$$(E_1^1+E_2^1+\ldots+E_{I_1}^1)^{N_1}(E_1^2+E_2^2+\ldots+E_{I_2}^2)^{N_2}(E_1^3+E_2^3+\ldots+E_{I_3}^3)^{N_3} \quad (1)$$

where $E_j^i$ represents the $j^{th}$ isotope of the $i^{th}$ element in the molecule. The $N_i$ superscript outside the parenthesis represents the number of atoms of the $i^{th}$ element. This will generate a combinatorial explosion in the number of terms for large molecules. The number of coefficients for the multinomial representing the $i^{th}$ element with $N_i$ atoms and Ii isotopes is given by:

$$C_{I_i}^{N_i} = \frac{(N_i + I_i - 1)!}{N_i!(I_i - 1)!} \quad (2)$$

and the coefficients of the multinomial are given by:

$$(E_1^i + E_2^i + \ldots + E_{I_i}^i)^{N_i} = \sum_{M_1+M_2+\ldots+M_{I_i}=N_i} \frac{N_i!}{M_1!M_2!\ldots M_{I_i}!} E_1^{iM_1} E_1^{iM_2} \ldots E_1^{iM_{I_i}} \quad (3)$$

The total number of terms T in the expanded polynomial of equation 1 is the number of terms in the product of the elemental multinomial coefficients and is given by:

$$T = C_{I_1}^{N_1} C_{I_2}^{N_2} C_{I_3}^{N_3} \quad (4)$$

which gives the number of possible masses in the isotopic fine structure.

For bovine insulin $C_{254}H_{377}N_{65}O_{75}S_6$ the number of possible terms is $1.56 \times 10^{12}$, which clearly precludes any brute force attack. In practice, one only needs a fraction of the terms since most of the terms are extremely unlikely. The least probable term is $^{13}C_{254}{}^{2}H_{377}{}^{15}N_{65}{}^{17}O_{75}{}^{35}S_6$ that has a probability of $0.2610 \times 10^{-2422}$ of occuring. The top 1000 terms represents 99.96% of the cumulative probability distribution.

An efficient method based on dynamic programming can be used to calculate the overall distribution of possible molecular weights given the isotopic distribution for each element. To apply dynamic programming, we first frame this calculation in the context of a Markov process $\{X_t\}_{t \in T}$ operating on a discrete state space S. The state transition probabilities are given by:

$$p_{ij} = P(X_{n+1} = j | X_n = i), n \geq 0, i, j \in X \quad (5)$$

This gives the probability of arriving at state Sj at step n+1, given that it was in state Si at step n. The state transition probabilities are required to have the following properties:

$$p_{ij} \geq 0 \quad (6)$$

$$\sum_{j=1}^{J} p_{ij} = 1, \forall i, j = 1, \ldots, J.$$

The initial state probabilities are given by:

$$\pi_i(0) = P(X_0 = i), i \in S \quad (7)$$

Figure 8:
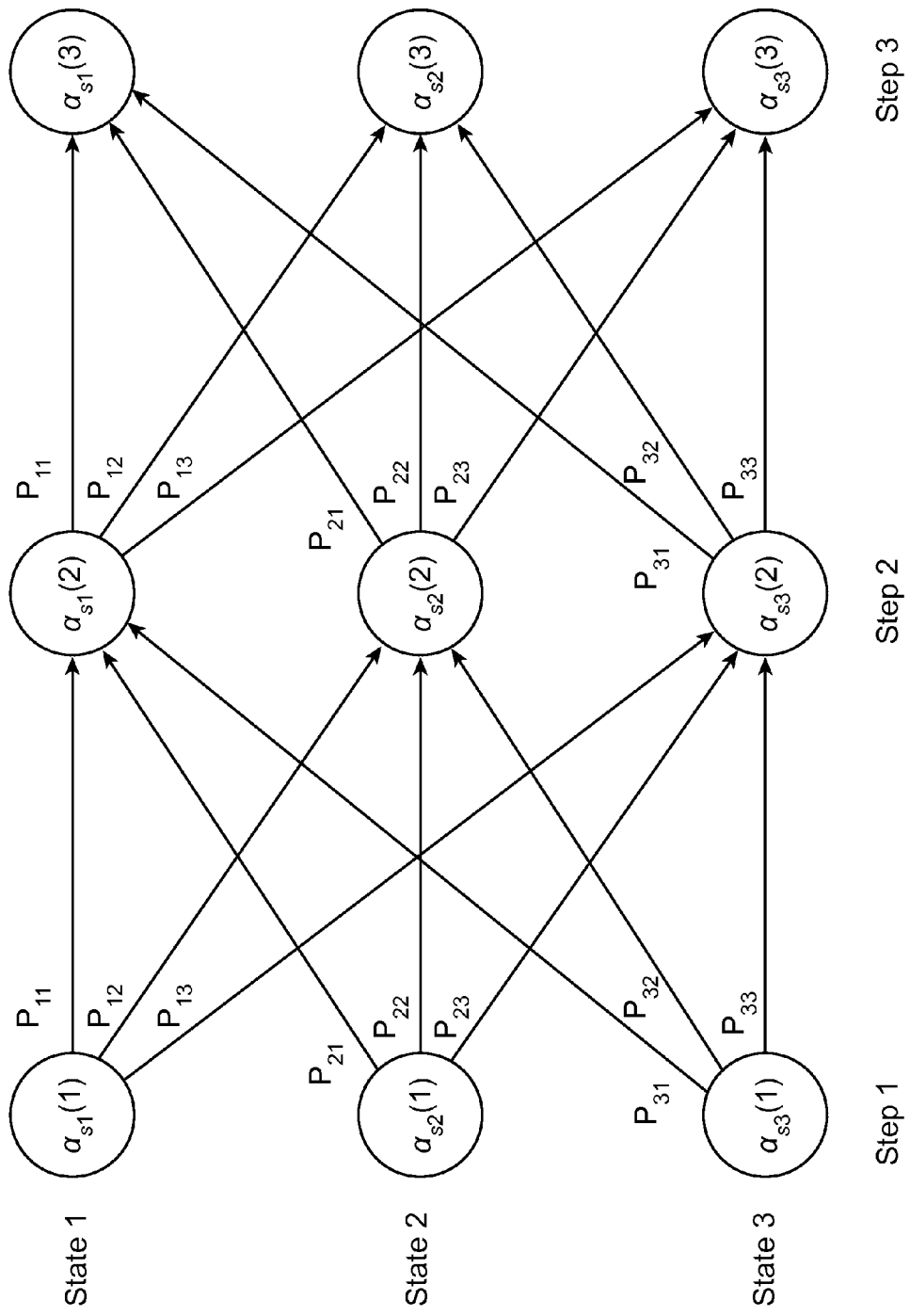
FIG. 8 shows a trellis for efficiently computing state probabilities.

The efficient way to calculate the probability of being in state Sj at step n+1 is to use a forward trellis algorithm. An illustration of this computation can be seen in FIG. 8.

The state probabilities for step n+1 are calculated by:

$$\alpha_{S_j}(n+1) = \sum_{i=1}^{N(n)} \alpha_{S_i}(n) p_{ij} \quad (8)$$

where $1 \leq j \leq N(n+1)$, $1 \leq n \leq T-1$. N(n) implies that the number of states is a function of step n.

The trellis algorithm gains its efficiency by collapsing the possible paths that can lead to a particular state. Only the state probabilities at step n along with the transition probabilities are used to calculate the state probabilities for the next step. This is known as a first-order Markov model or chain.

In the context of calculating the isotope distribution, the states are the set of unique molecular masses that can exist at each step. At each step, all isotopes of one atom of a particular element are added, i.e., $$(E_1^i + E_2^i + \ldots + E_{I_1}^i)$$

which means that the state transition probabilities are non-stationary since they depend on the isotope distribution of the particular element being added. The Markov chain can be thought of as the sequence of adding elements with all associated isotopes at each step. The length of the chain is the number of elements in the molecule. The number of states at each step is also non-stationary since particular combinations of isotopes lead to unique masses. The states at step n+1 is the set of unique masses computed by adding the mass of any state at step n with any isotope of the element being added. The probabilities of these states are given in equation 8. These states are then either pruned or combined to reduce computational complexity and this process is called state reduction.

II. State Reduction

Most Probable Exact Masses

Keeping the distribution of all exact masses becomes impractical for all but the smallest molecules. If one is interested in the exact masses of the most probable isotope mass combinations, as is typically the case, then the states with lowest probabilities are eliminated. This is done by computing all states for step n+1, sorting these states based on probabilities, and then keeping only the top $N_{max}$ most probable states where $N_{max}$ is user specified. Once all the elements have been added at the last step, isoDalton returns the exact masses of the Nmax most probable isotopic mass combinations. The "true" probabilities of these exact masses are only approximations since eliminating states prunes potential path combinations that affect probability values. Increasing Nmax will reduced this error.

Exact Probability Distribution

If a user is interested in viewing the overall probability distribution of near integer separated values, then close mass values can be combined as follows. Let $M_{old1}$ and $M_{old2}$ be the masses of states $S_i$ and $S_j$ that are the closest together in terms of mass values and let $P_{old1}$ and $P_{old2}$ be their respective probabilities. Then a new state is created that has mass and probability of:

$$M_{new}(M_{old1}P_{old1} + M_{old2}P_{old2}) \quad (9)$$

$$P_{new} = P_{old1} + P_{old2} \quad (10)$$

For a particular step n, the states are combined in this fashion until there are $N_{max}$ states. Combining states in this manner results in a probability distribution of $N_{max}$ masses that are the center of masses of the isotopic fine structure exact masses. These are exact probabilities for these "center of mass" weights since they sum to 1 as expected of a probability distribution.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A computer-implemented method for confirming the nucleotide sequence of an oligonucleotide comprising:
   a) inputting the nucleotide sequence of an oligonucleotide;
   b) executing, using a computer, an algorithm that provides the predicted molecular formulas of fragments of the oligonucleotide, wherein the algorithm provides predicted molecular formulas for all a-B, a, b, c, d, w, x, v and z fragments of the oligonucleotide, where the bonds broken to obtain said fragments are defined in FIG. 1;
   c) predicting exact m/z values of said fragments using said molecular formulas; and
   d) comparing the predicted exact mass to m/z values of c) to experimentally-obtained m/z values obtained by analysis of said oligonucleotide by tandem mass spectrometry to determine if the predicted exact mass to m/z values correlate with the experimentally-obtained m/z values.

2. The method of claim 1, further comprising confirming the identity of said oligonucleotide if said predicted exact m/z values correlate with the experimentally-obtained m/z values.

3. The method of claim 1, wherein the inputting comprises inputting the sequence of oligonucleotide that contains one or more nucleotide analogs.

4. The method of claim 1, wherein the inputting comprises inputting a label moiety or linker that is part of oligonucleotide.

5. The method of claim 1, wherein said comparing step comprises comparing the predicted m/z values for all a-B, a, b, c, d, w, x, y and z fragments of the oligonucleotide to experimentally-obtained m/z values.

6. The method of claim 1, wherein said experimentally-obtained m/z values are within a range of m/z values.

7. The method of claim 1, wherein said experimentally-obtained m/z values are within a range of in the range of 100 to 5000 mass units.

8. The method of claim 1, wherein the comparing step results in an editable data file comprising a table.

9. The method of claim 8, further comprising generating a human-readable report base on said table.

10. The method of claim 9, further comprising looking at the report in a graphical format, identifying any overlapping peaks, editing the data file and re-performing the comparing step based on the edited data table.

11. The method of claim 1, further comprising synthesizing an oligonucleotide;
    analyzing said oligonucleotide using tandem mass spectrometry; and performing steps a), b) and c) using the nucleotide sequence of said oligonucleotide and data obtained from said analyzing.

12. A physical computer readable medium comprising programming for:
    a) inputting the nucleotide sequence of an oligonucleotide;
    b) predicting, using a computer, the molecular formulas of fragments of the oligonucleotide using an algorithm, wherein the algorithm provides predicted m/z values for a-B, a, b, c, d, w, x, v and z fragments of the oligonucleotide, where the bonds broken to obtain said fragments are defined in FIG. 1;
    c) predicting exact m/z values of said fragments using said molecular formulas; and
    d)) comparing the predicted exact mass to m/z values of c) to experimentally-obtained m/z values obtained by analysis of said oligonucleotide by tandem mass spectrometry to determine if the predicted exact mass to m/z values correlate with the experimentally-obtained m/z values.

13. The physical computer readable medium of claim 12, wherein said comparing step comprises comparing the predicted m/z values for all a-B, a, b, c, d, w, x, y and z fragments of the oligonucleotide to experimentally-obtained m/z values.

14. The physical computer readable medium of claim 12, wherein said physical computer readable medium is present on a computer and operably linked to a processor for executing said programming.

15. A system comprising:
    an oligonucleotide synthesizer;
    a tandem mass spectrometer; and
    a computer comprising the physical computer readable medium of the claim 12.

* * * * *

UNITED STATES PATENT AND TRADEMARK OFFICE
CERTIFICATE OF CORRECTION

PATENT NO. : 8,486,707 B2
APPLICATION NO. : 13/093723
DATED : July 16, 2013
INVENTOR(S) : Zoltan Timar et al.

It is certified that error appears in the above-identified patent and that said Letters Patent is hereby corrected as shown below:

In the Claims:

In column 11, line 35, In Claim 1, after "x," delete "v" and insert -- y --, therefor.

In column 12, line 8, In Claim 7, after "range of" delete "in the range of".

In column 12, line 30, In Claim 12, after "x," delete "v" and insert -- y --, therefor.

Signed and Sealed this
Seventeenth Day of September, 2013

Teresa Stanek Rea
*Deputy Director of the United States Patent and Trademark Office*